United States Patent
Kreuwel et al.

(10) Patent No.: US 6,764,859 B1
(45) Date of Patent: Jul. 20, 2004

(54) DEVICE AND METHOD FOR MIXING MAGNETIC PARTICLES WITH A FLUID

(75) Inventors: Hermanus Johannes Maria Kreuwel, Schijndel (NL); Emiel Gerebern Maria Verwimp, Geel (BE)

(73) Assignee: bioMerieux, B.V. (NL)

( * ) Notice: Subject to any disclaimer, the term of this patent is extended or adjusted under 35 U.S.C. 154(b) by 0 days.

(21) Appl. No.: 10/031,222

(22) PCT Filed: Jul. 14, 2000

(86) PCT No.: PCT/EP00/06789
§ 371 (c)(1),
(2), (4) Date: Jun. 4, 2002

(87) PCT Pub. No.: WO01/05510
PCT Pub. Date: Jan. 25, 2001

(30) Foreign Application Priority Data

Jul. 19, 1999 (EP) .......................................... 99202354

(51) Int. Cl.$^7$ .............................. G01N 1/34; G01N 1/38
(52) U.S. Cl. ........................ 436/178; 436/94; 436/526; 209/217; 209/223.1; 209/225; 209/226; 209/227; 210/222; 210/695; 366/273; 366/274; 422/65; 422/99; 422/101; 435/6; 435/287.1; 435/287.2; 435/287.3; 536/25.4
(58) Field of Search ........................ 536/25.4; 366/273, 366/274; 209/213–217, 225–227; 435/287.1, 287.2, 287.3, 6; 436/526, 178, 94; 422/99, 101, 63–67; 210/695, 222

(56) References Cited

U.S. PATENT DOCUMENTS

| 3,985,649 | A | * | 10/1976 | Eddelman | 210/695 |
| 5,558,839 | A | | 9/1996 | Matte et al. | 422/101 |
| 5,770,461 | A | | 6/1998 | Sakazume et al. | 436/526 |
| 5,897,783 | A | * | 4/1999 | Howe et al. | 210/695 |
| 6,040,192 | A | * | 3/2000 | Tuunanen | 436/177 |
| 6,281,008 | B1 | * | 8/2001 | Komai et al. | 435/306.1 |
| 6,335,166 | B1 | * | 1/2002 | Ammann et al. | 435/6 |

FOREIGN PATENT DOCUMENTS

| EP | 0691541 A2 | 10/1996 |
| WO | WO 96/26011 | 8/1996 |

OTHER PUBLICATIONS

International Search Report, PCT/EP00/06789, mailed Jul. 11, 2000.
International Preliminary Examination Report, PCT/EP00/06789, mailed Oct. 24, 2001.

* cited by examiner

Primary Examiner—Jan M. Ludlow
(74) Attorney, Agent, or Firm—Myers Bigel Sibley & Sajovec PA

(57) ABSTRACT

This invention relates to the use of magnetic or magnetizable particles, and, in particular, to methods of mixing magnetic or (super)paramagnetic particles efficiently with a fluid and the separation of the magnetic particles from a fluid, optionally followed by resuspension of the particles in another fluid. The present invention provides a method of mixing, in one or more container(s), magnetic or (super)paramagnetic particles with a fluid, using more than one magnets, whereby the containers are subjected to magnetic fields with different and changing directions by moving the magnets with respect to the position of the container(s) and/or by moving the containers with respect to the positions of the magnets. The invention further provided a device for doing the same. Preferably the holders for the containers and the magnets in the device are placed in intervening array geometrics and the magnets are placed in line in such a way that all magnets that are in line have their poles oriented in the same direction, and that all magnets in a neighboring line have their poles oriented in the reverse direction with respect to the poles of the magnets in the first line.

42 Claims, 2 Drawing Sheets

Side view

Top view

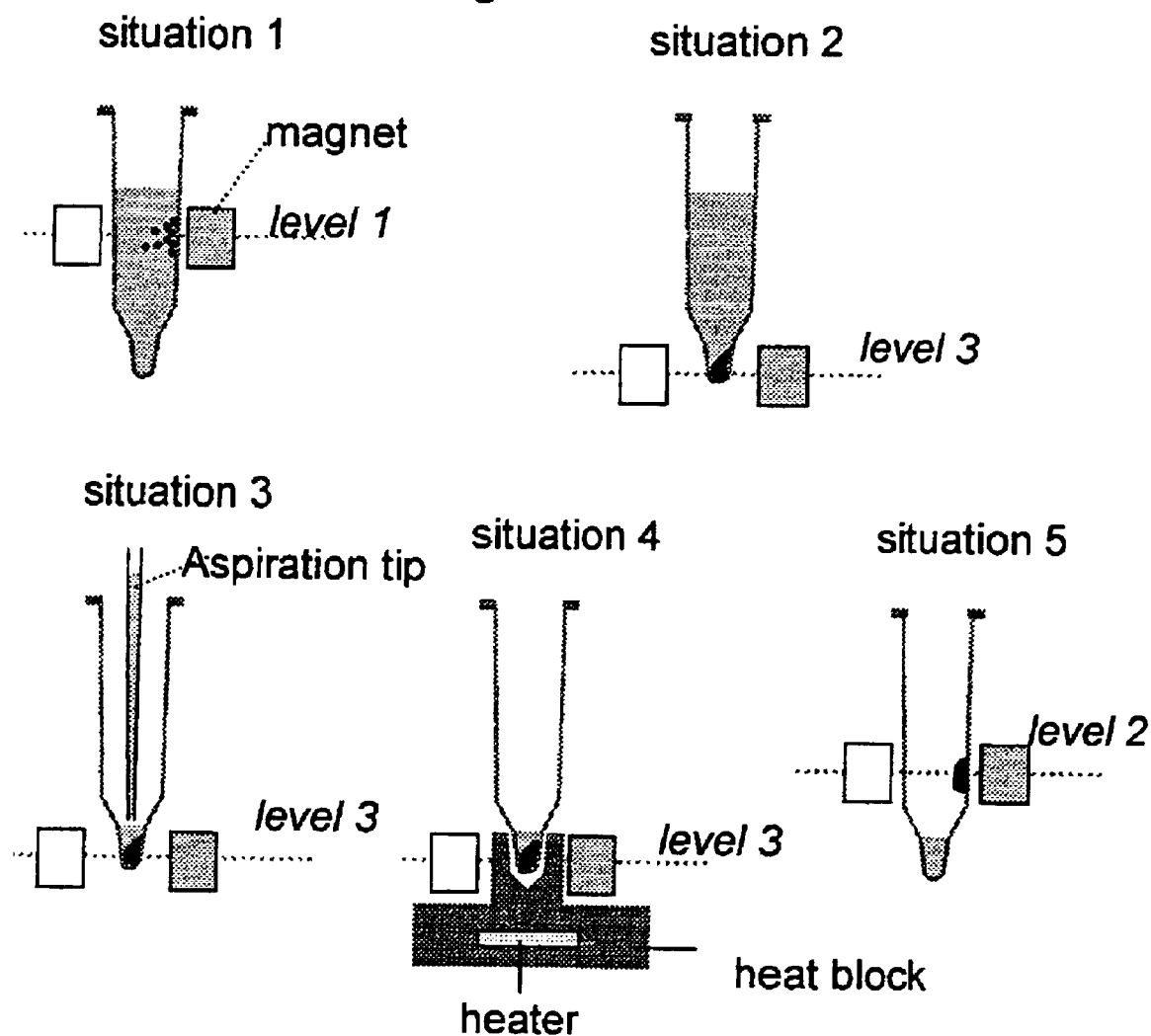

DEVICE AND METHOD FOR MIXING MAGNETIC PARTICLES WITH A FLUID

RELATED APPLICATIONS

This application claims priority from International PCT Application Serial No. PCT/EP00/06789 filed Jul. 14, 2000, which claims priority from EP Application Ser. No. 99202354.9 filed Jul. 19, 1999. The international application was published in English under PCT Article 21(2). The contents of these applications are hereby incorporated by reference as if recited in full herein.

FIELD OF THE INVENTION

This invention relates to the use of magnetic or magnetizable particles, and, in particular, to methods and related devices used in mixing magnetic or (super)paramagnetic particles efficiently with a fluid and the separation of the magnetic particles from a fluid, optionally followed by resuspension of the particles in another fluid.

BACKGROUND OF THE INVENTION

Magnetic particles are often used in separation processes. There are many biological assay methods and purification methods in which magnetic particles are used. For example, immuno assay methods, nucleic acid hybridization assays and the like. Magnetic particles can also be used in purification methods, to isolate particular compounds, proteins, nucleic acids, from the material in which they were contained. The particles can be used to separate certain components from a mixture, for example, because they are coated with a reagent with a specific affinity for the component. Magnetic particles can be drawn to, for example, the wall of a container in which the fluid with the magnetic particles was contained and the fluid can be removed and, optionally, be replaced with another fluid. Thus, the particles can be mixed with the fluid from which the specific component is to be removed, the component will bind to the magnetic particle, and a magnet can be used to separate the particles with the component from the remainder of the mixture in the fluid. Optionally the magnetic particles can be washed, and can be separated in another fluid. Or the component can be removed from the particles again into another fluid.

The use of magnetic particles for purifying a nucleic acid (NA) target from a biological sample is well known.

Purification methods for nucleic acid using magnetic particles have for example been described in EP757106 (Toyobo) and WO 96/41811 (Boehringer Mannheim). In these applications methods described wherein a sample solution containing nucleic acid is treated with a chaotropic substance to release the nucleic acid. After releasing the NA from the biological entity in the lysis buffer, the NA is bound to the magnetic particles. Both particles coated with a target-specific probe as well as particles having a metal oxide coating (e.g. silica), giving a generic binding of all NA contained in the sample are used for this purpose. After binding the target, interfering components such as cell debris, enzymes, proteins anti-coagulants and salt are removed by washing the magnetic particles in a (set of) wash buffer(s). Finally, the purified NA is released from the particles by mixing the particles in a small volume of elution buffer. This process is called elution since it is the nucleic acid that is eluted from the particles.

For efficient washing and elution the magnetic particles need to be well dispersed and mixed in the relevant buffers. In general, this washing and elution process may be hampered by the aggregation or clogging of the magnetic particles either caused by the adsorption on the magnetic particles of specific components in the lysed sample (e.g. g nomic DNA) or by residual magnetic dipole fields induced in the particles. In particular, the use of silica coated (magnetic) particles with samples that contain significant amounts of genomic DNA (whole blood, sputum, tissue), results in a tight pellet that is difficult to process.

Well-known methods for mixing (magnetic) beads in a liquid buffer are vortexing, sonification or pipetting. These methods however are difficult to automate, and/or give risk of sample to sample contamination by aerosol generation or they may degrade the NA target. Furthermore, these methods are not well suited for very small volumes of liquid (typically 0.01 ml) as may be required for the elution process.

A method and apparatus for separating and resuspending superparamagnetic particles is disclosed in WO 91/09308 (Diatec instruments).

In this application it was disclosed that superparamagnetic particles may be aggregated and resuspended by subsequent application of different magnetic fields. First and second applications of the magnetic field could be provided with the same magnet, which was then rotated around the container containing the particles to a different location. Two spaced opposed electromagnets, however, could also be used. These electromagnets were energized alternately to produce the first and second magnetic fields that keep the particles in suspension and mix them with the fluid in which they were contained. A method for the separation of magnetic particles from a fluid is disclosed in U.S. Pat. No. 3,985,649. The particles may be separated from a fluid by bringing the particles into close proximity with a magnet and moved trough the liquid along the wall of a container. They may even be moved out of the liquid in this way and can be transported to a second container. In U.S. Pat. No. 4,988,618 a device is described for use with assays wherein multiple small volume samples are tested at the same time. These type of assay can be performed in, for example, microtiter plates. Magnetic microparticles are present in each well of the microtiter plate. The device thus has multiple orifices and the orifices are each surrounded by multiple permanent magnets, preferably four. The resulting structure of magnets and orifices is rigid; the magnets are not intended to be moved and are mounted in fixed relations with respect to themselves and to the base of the device. All magnets are aligned and the field orientation of the magnets may be such that all magnets have the same field direction or neighboring magnets have opposite field directions. The magnet orientation thus results in four spot attraction sites per orifice. The magnets are purely meant for separation purposes. It is disclosed in the patent that the device may further comprise means for agitating the reagents within the containers.

BRIEF SUMMARY OF THE INVENTION

The present invention relates to a method and device, which allows efficient mixing of magnetic or magnetizable particles in a fluid, and optionally separation of the particles from said fluid. Use is made of magnetic field of opposite and changing directions. It has been found that, when magnetic or magnetizable particles in a fluid are subjected to these magnetic fields, the particles are, under the influence of the field, efficiently contacted with the fluid. Such particles normally may tend to form a clot, which can prevent efficient mixing with a fluid. It has been found that, by subjecting the container in which the fluid and the particles are comprised, to magnetic fields of different and changing directions, the particles are efficiently separated from each other and drawn trough the fluid in such a way that a very efficient mixing process occurs. The method allows efficient mixing of particles with even very small fluid volumes. The method of the invention therefore has the advantage that it may save in, for example, washing fluids and may allow the reduction of the volume of fluid needed. Thus, for example is isolation procedures, the method of the invention allows the purification of reagents in high concentrations. Beside, whereas prior art methods can be laborious and time consuming, the method is fast and easy to perform.

The method and device according to the invention are especially suitable for use with isolation procedures, where, usually an ingredient is to be isolated in rather pure form from a relatively large volume of sample fluid, and concentrated into a smaller volume of another fluid to be suitable for further use. In the case of a method for the isolation of nucleic acid such further use may be a nucleic acid amplification method or an assay for the detection of nucleic acid or both.

Thus, provided with the invention is a method of mixing, in one or more container(s), magnetic or (super) paramagnetic particles with a fluid, using more than one magnets, whereby the containers are subjected to magnetic fields with different and changing directions by moving the magnets with respect to the position of the container(s) and/or by moving the containers with respect to the positions of the magnets.

With "mixing" in this context is meant that the particles and the fluid are brought in close contact. Mixing thus, means "contacting" in a very efficient manner, such as when particles would be washed or reacted with components present in the fluid. Mixing, in this context, does not necessarily provide a homogeneous mixture after the process is finished. The particles may, when the magnets are removed, segregate to the bottom of the container in which they are comprised or may be held to the wall of the container in a particular location by the magnets. The mixing process can for example be used to wash the particles or to react the particles with a component of the liquid, or to bind a component of the liquid to a reagent coated on the particles. Likewise, the mixing process may result in the elution of a certain component originally present on the particles into the surrounding liquid. The method of the invention is applicable in each of these processes and provides an efficient rapid and convenient way of contacting magnetic or magnetizable particles with a volume of a certain fluid.

The present invention thus provides a generic method for mixing magnetic particles with a fluid almost independent of their level of pelleting/aggregation. The method further allows releasing of reagents bound to the particles, for example nucleic acid, from the particles and concentration into a small volume. The method is easy to automate and well suited for high throughput formats. It minimizes the risk of contamination by droplets or aerosols.

BRIEF DESCRIPTION OF THE FIGURES

FIG. 4: Device wherein the magnets can also be moved in a vertical direction so as to be positioned at different heights with respect to the walls of the containers and the containers are tube-shaped vessels provided with a tip for holding small liquid volumes.

Figure 1:
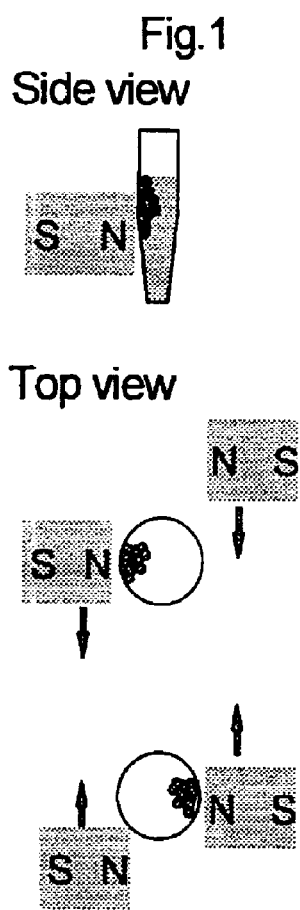
FIG. 1: The basic concept of an array according to the invention.

During a washing (or elution) cycle the (aggregated) particles are dragged through the liquid from left to right by placing a first magnet close to the outside right wall of the vessel and subsequently withdraw this first magnet and simultaneously place a second magnet close to the opposite (left) wall of the vessel in order to drag the particles into the opposite direction. The present invention furthermore provides a device for performing said method.

The device according to the invention comprises means for holding the containers and more than one magnets and means for moving said magnets with respect to the position of said containers and/or means for moving said containers with respect to the position of said magnets in such a way that the containers are subjected to magnetic fields with different and changing directions.

Preferably the magnets are moved with respect to the containers.

The containers may have any convenient shape. Any vessel, suitable for holding a fluid sample in which magnetic particles are dispersed can be used. Preferably the vessels are suitable for holding small liquid samples. For example, they may be Eppendorf cups, PCR containers or micro-titer plate strips).

The magnets may be placed in different geometries with respect to the containers. Any geometry which allows the movement of the magnets with respect to the position of the containers or the other way around, and which will result in magnetic fields of different and changing polarity in each container can be used.

It was found that this washing (or elution) process become particular efficient with the two magnets arranged in such a way that they strongly repel each other (by facing each other with similar poles N—N or S—S). Due to this arrangement the magnetic field lines in the area in the vessel where the magnetic beads are located show a strong and sudden change in direction during each cycle. When the container is placed between two magnets that strongly repel each other because their similar poles are facing each other (N—N or S—S) the slightest movement of either one of the magnets or of the container with respect to each other will result in sudden strong changes of the magnetic field to which the particles in the container are subjected. It has been found that this results in a very efficient way of mixing the particles with the fluid, even when the particles as such tend to form a clot or had already formed a clot within the fluid.

The magnets are preferably arranged in such a way that each magnet repels each of its neighboring magnets.

The magnets may be placed in line in such a way that magnets of opposite polarities can be moved back and forth on straight parallel paths along opposite sites of each container in such a way that the direction of the magnetic field in each container is repeatedly reversed.

This may advantageously be achieved by placing the magnets in line in such a way that all magnets that are in line have their poles oriented in the same direction, and that all magnets in a neighboring line, that is on the other side of the containers next to the first line of magnets, have their poles oriented in the reverse direction with respect to the poles of the magnets in the first line.

When the magnets are moved, this may result in the containers being repeatedly placed between two magnets that face each other with the same pole.

The magnets and containers may be placed in parallel rows and the rows of magnets can be moved in opposite directions alongside the rows of containers.

But, of course, based on the basic concept of the method of the invention other geometries can likewise be devised.

The basic concept of an embodiment of a device according to the invention wherein the magnets are movable with respect to the containers is illustrated in FIG. 1. The magnetic particles are in a liquid buffer contained in a vessel. The (aggregated) particles are dragged through the liquid from left to right and v.v. by translating a set of at least two magnets arranged such that the magnetic field induced in the vessel changes polarity upon each movement of the magnets.

The method can be used with more containers and magnets. Thus the method and device according to the invention allow for batch-wise processing of several vessels simultaneously. The method and device according to the invention are especially suitable for treating a large number of fluid volumes in each of their respective containers at the same time.

In a preferred embodiment of the device according to the invention the containers and the magnets are placed in intervening array geometries. This layout allows the use of the method of the invention to give a high throughput format.

Figure 2:
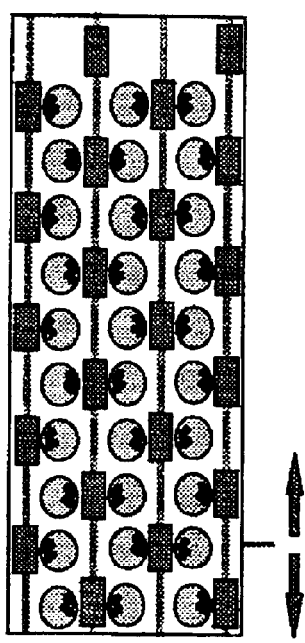
FIG. 2: Device wherein the holders for the containers and the magnets are placed in intervening array geometrics and the magnets are placed in line in such a way that magnets of opposite polarities can be moved back and forth on straight parallel paths along opposite sites of each container in such a way that the direction of the magnetic field in each container is repeatedly reversed.

An embodiment wherein the containers and the magnets are placed in intervening array geometries is illustrated in FIG. 2. The vessels (e.g. Eppendorf cups, PCR containers or micro-titer plate strips) are placed in an array geometry with the magnets fixed to a second array that translates with respect to the vessels.

In this way a large series of samples is processed simultaneously. Addition and aspiration of liquids may be by hand or by an automated multi-tip dispenser instrument as know in the art.

Figure 3:
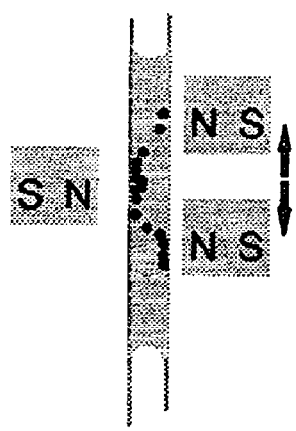
FIG. 3: Device wherein the containers are part of a closed system, e.g. a tube.

The method of the invention may also be used with a closed system. That is, a system wherein the liquid, for example, is not contained in a vessel, but in a tube. Thus, with containers, as used with the method of the invention, not only containers used in batch wise processes are meant but also containers used in closed systems, such as tubes and the like. Such an alternative embodiment of a device according to the invention illustrated in FIG. 3. The particles and liquid are not contained in a vessel but in a tube, allowing processing the particles in a closed system.

Depending on the exact intended use of a device of the present invention several modifications and variations on the above-described theme are possible. For example, the shape of the container may be modified and further modifications as to the location of the magnets with respect to said containers can be made as well.

A device according to the present invention is especially suitable for use with methods for the purification of, for example, nucleic acid from biological starting material.

For a specific purpose the device can be further modified to match the intended use.

The adjustments may result in better ways for separating the particles from the liquid. The device may also be adjusted in such a way that it can be used with different sample fluid volumes.

In a preferred embodiment according to the invention the magnets can not only be moved with respect to the position of the containers but can also be moved in a direction along the walls of the containers (which would be vertical, when the containers are in an upright position).

In this way, the position of the magnets can be adjusted according to the volume of the fluid in the containers. Thus, when there is only a very small fluid volume to be mixed with the particles the magnet with be in a position that is lower than the position it will have when there is a larger volume of fluid in the same container.

The fact that the magnets can be moved in a vertical direction has the additional advantage that the magnets can now also be used to draw the particles to the lower part of the container, even when a bigger fluid volume is used. Thus, this allows the removal of a large part of the fluid volume, for example by a pipettor, while the magnet holds down the particles.

Optionally, the magnets, when they can be moved in a vertical direction along the walls of the containers, can also be used to draw the particles alongside the wall of the container till a position above the surface of the fluid. In that way the particles can be separated from the fluid and the remaining fluid may be removed from the container or, for example, be replaced by another fluid after which the particles may be drawn down below the liquid level and mixed with the new fluid using the magnets.

It is evident that the design of the device allows many variations in the methods of its use and all fall within the scope of the invention.

The use of the movement of the magnets in a vertical direction is illustrated in FIG. 4.

To allow the use of the device with a procedure involving the subsequent treatment of the particles with several liquids in different volumes and achieve an efficient mixing and separation of the particles with/from the respective fluids, adjustments can be made to the containers as well.

If a large container is used with a very small fluid volume the problem may arise that the particles can no longer be contacted with the fluid, simply because the fluid volume is more or less spread out over the bottom of the container and doesn't even cover the particles.

Thus, containers can be devised that can be used with different liquid volumes and still allow efficient mixing of the fluid volumes with the particles. Such containers and the use thereof are likewise part of the present invention.

To allow the use of fluids considerable different volume a container can be used that comprises a part that is suitable for containing small fluid samples, while this part is connected to a part that is suitable for containing large volume samples. An example of such a container is illustrated in FIG. 4.

The multi-purpose container as depicted in FIG. 4 is provided with a tip with a relatively small diameter suitable for containing small volume samples, while the part on top of the tip is suitable for containing larger volume samples.

As indicated in FIG. 4 this container is suitable for using the device with small and large fluid volumes and the height of the magnets with respect to the container can be adjusted accordingly.

Moreover, the tip allows the collection of the particles from a large volume sample by moving the magnets in the downward orientation. The major part of the liquid can then be removed from the container without accidentally removing any of the particles.

A device according to the invention is especially suitable for use in a method for the isolation of nucleic acid from biological samples.

A typical method for the isolation of nucleic acid is the method as devised by R. Boom et al., as disclosed in EP 389063.

The "Boom method" involves the treatment of the biological material with a lysis buffer containing a chaotropic substance such as guanidine-isothiocyanate and a siliceous solid phase. The siliceous solid phase may be provided in the form of magnetic silica particles. The nucleic acid released from the material by the lysis buffer will adhere to the (magnetic) siliceous particles. Thus, the particles and the biological material in the lysis buffer should be thoroughly contacted with each other, which is where the use of a device according to the method would come in. The particles with the nucleic acid adhered thereto can subsequently be separated from the remainder of the sample using a magnet (which can also be done with a device according to the invention provided that it is adapted for that purpose). Subsequently the nucleic acid containing particles should be washed, which requires the mixing of the particles with a washing buffer. This is another function that may be performed by the device according to the invention. The particles are then removed from the washing liquid and contacted with an elution buffer (again, thorough contact between the particles and the elution buffer is required) and the nucleic acid is thus released from the particles into the elution buffer. In general, liquid volumes required for washing will be about 10 times larger than for elution. A typical volume for washing (per vessel per wash step) is 0.2–0.5 ml. The typical volume for elution buffer is 0.010/0.050 ml.

The embodiment of the device wherein the magnets can be moved in the vertical direction as well and containers are used that have a tip for the use of smaller liquid volumes is especially suitable for use with the so-called "Boom method" for the isolation of nucleic acid as described above.

When the device would be used with a method like the Boom method this can be performed with the following procedure:

A typical volume required for a washing step would be 0.2 to 0.5 ml, which is a relatively large volume. Therefore, during washing the magnetic particles are in the upper part of the vessel (level 1, FIG. 4 situation 1). However, for most applications the nucleic acid target needs to be concentrated in a buffer volume of typically 10 to 50 µl. Such small liquid volumes are hard to handle. It is difficult to control the size of such a small volume as well as to manipulate it is a vessel in combination with magnetic particles to form a suspension for performing bound-free steps.

FIG. 4 shows a method that overcomes the above difficulties.

After completing the washing procedure the particles are captured at the side of the vessel wall (level 1, situation 1) and the wash liquid is aspirated with a pipette tip. Next, the vessel is filled with fresh elution buffer (about 0.2 ml) and the magnetic particles are transported down to the lower end of the vessel (level 3) by bringing the magnets down (situation 2). Transport of particles can be accelerated by translating the magnet array as is done during washing as it moves downward. The composition of the ET buffer is such that no nucleic acid is released from the silica as long as the buffer temperature is not above RT.

Next, while aspirating, the tip is introduced into the vessel until its lower end is at a level that corresponds to the required volume of ET buffer (e.g. 10 µl, see situation 3).

Next, a heat block is brought into contact with the vessel to heat up the temperature of the buffer to 55–60° C. (situation 4).

Next, the actual elution procedure starts by translating the magnets horizontally as during the washing procedure, but now at level 3. Preferably, during elution, the heat block remains in contact with the vessel to keep the temperature of the elution buffer at 55–60° C.

Finally, after completing the elution, the heat block is moved away from the containers (down) and the magnets are moved up to level 2 (situation 5) to withdraw the particles from the elution buffer that is now ready for further processing (amplification, sequencing.) Preferably, in order to allow the heat block to contact the vessel during elution without disturbing the elution process (situation 4), the heat block has a special design that accounts for the dimensions of the magnetic array as well as for the shape of the vessel. The heat block preferably is produced from a material that is non-magnetic. For example, the heat block is produced from aluminum and contains a ceramic heater element as is known from the state of the art.

Thus, it is illustrated how the device can be used to automate and speed up existing procedures, that now have to be perform, either by hand or in more complicated automated devices.

Of course, the use of a device according to the invention will find its application in many biological assays or purification processes.

What is claimed is:

1. Method of mixing, in one or more container(s), magnetic or (super) paramagnetic particles with a fluid, using at least two magnet arrays with a corresponding container array disposed between adjacent magnet arrays to form an intervening array geometry, wherein each magnet array comprises a plurality of spaced apart magnets, whereby the containers are subjected to magnetic fields with different and changing directions by moving the magnets in the adjacent magnet arrays with respect to the position of the container(s) in the corresponding container array and/or by oscillating the containers with respect to the positions of the magnets.

2. Method according to claim 1, wherein the containers, by oscillating the containers or moving the magnets in first and second adjacent magnet arrays, are subjected to magnetic fields of opposite polarity.

3. Method according to claim 1, wherein, as a result of moving either the magnets or the containers, the magnetic or (super) paramagnetic particles in the fluid in respective containers are repeatedly moved between two corresponding magnets that face each other with the same pole, the corresponding magnets being disposed in adjacent magnet arrays on opposing sides of the containers with one held in a first magnet array and the other held in a second magnet array.

4. Method according to claim 1, wherein the magnets in a respective magnet array are moved in concert with respect to the position of the containers and/or the containers in a respective container array are moved in concert with each other with respect to the position of the magnets in such a way that the magnetic or (super)paramagnetic particles are moved through the fluid to one side of the container by bringing a first magnet with its magnetic pole close to the wall of the container and, subsequently are moved to the opposite side by bringing a second magnet close to the opposite wall of the container, whereby said second magnet has the same magnetic pole as the first magnet in such a way that the direction of the magnetic field in each container is repeated reversed.

5. Method according to claim 1, wherein the magnets of respective magnet arrays are moved in concert with respect to the containers.

6. Method according to claim 1, further comprising dispersing the magnetic or (super)paramagnetic particles in a clotted or aggregate configuration into the fluid.

7. Method according to claim 6, further comprising mixing the fluid sufficiently to cause the clotted and/or aggregate of magnetic particles to separate and/or disperse to thereby promote mixing with the fluid.

8. Method according to claim 1, further comprising linearly translating magnets in respective magnet arrays about substantially parallel paths so that the magnets in each array move forward and rearward in concert and so that adjacent arrays of magnets move in opposing directions on opposite sides of a respective container array in such a way that a direction of the magnetic field in each container is repeatedly substantially reversed.

9. Method according to claim 1, wherein the containers are oscillated by moving the containers in the container array in concert back and forth magnet arrays.

10. Method according to claim 1, wherein the at least two magnet arrays comprise first and second magnet arrays with the first container array disposed substantially centrally spaced therebetween, with the first and second magnet arrays and the container array being arranged in substantially parallel rows, with the first magnet array and the second magnet array configured to move in opposite directions alongside the row of containers to provide the mixing.

11. Method according to claim 1, wherein the at least two magnet arrays comprise first and second arrays with the first container array disposed substantially centrally spaced therebetween, and wherein the mixing is carried out by oscillating the containers in the container array, the oscillating step comprises moving the containers in the container array so that containers in the first container array are repeatedly exposed to different magnetic fields provided by the first and second magnet arrays.

12. Device for mixing magnetic or (super) paramagnetic particles in containers with a fluid, said device comprising means for holding said one or more containers in at least one container array having a plurality of spaced apart containers and a plurality of magnet arrays, a respective one disposed on opposing sides of the at least one container array, each magnet array comprising a plurality of spaced apart magnets, the magnet arrays configured and aligned in the device so as to cooperate with the at least one container array to concurrently expose the containers therein to different and changing magnetic field directions and means for horizontally moving said magnets with respect to the position of said containers and/or means for horizontally oscillating said containers with respect to the position of said magnets in such a way that the containers are subjected to magnetic fields with different and changing directions.

13. Device according to claim 12, the device being provided with a heat block that is positioned in such a way that it can be moved into close proximity with the containers so as to warm their contents, and moved away again.

14. Device according to claim 13, wherein the heat block is positioned underneath the containers and has wells which enclose the tips of the containers when the heatblock is brought into close proximity with the container.

15. Device according to claim 12 wherein each magnet in a respective magnet array is oriented in such a way that it repels each of its neighboring magnets.

16. Device according to claim 12, wherein magnets in first and second magnet arrays can be moved back and forth in concert on straight parallel paths along opposite sites of a corresponding first container array in such a way that the direction of the magnetic field in each container in the first container array is repeatedly reversed.

17. Device according to claim 12, wherein the magnets in first and second magnet arrays are placed in line in such a way that all magnets that are in line in the first array have their poles oriented in the same direction, and that all magnets in a neighboring second magnet array line have their poles oriented in the reverse direction with respect to the poles of the magnets in the first magnets array line.

18. Device according to claim 12, herein the magnets can also be moved in a vertical direction so as to positioned at different heights with respect to the walls of the containers.

19. Device according to claim 12, wherein the containers are part of a closed system whereby the containers are adapted to remain in position in the device and serially receive and expel fluid samples.

20. Device according to claim 12, wherein the containers are tube-shaped vessels provided with a tip with a smaller diameter.

21. Device according to claim 12, wherein, in operation, the device is configured to isolate nucleic acid.

22. Device according to claim 12, wherein the device is configured to disperse magnetic or (super) paramagnetic particles in a clotted or aggregate configuration in the fluid.

23. Device according to claim 22, wherein, in operation, the device is configured to cause the clotted and/or aggregate of magnetic particles to separate to thereby promote mixing with the fluid.

24. Device according to claim 12, wherein said device comprises means for moving said magnets, said means for moving the magnet being configured to linearly translate magnets in respective magnet arrays about substantially straight parallel paths so that the magnets in each array move forward and rearward in concert and so that adjacent arrays of magnets move on opposite sides of a respective container array so that the magnetic field direction in each container is repeatedly reversed.

25. Device according to claim 12, wherein said device comprises means for oscillating the containers by moving the containers in the at least one container array in concert back and forth.

26. Device according to claim 12, wherein the plurality of magnet arrays comprise first and second magnet arrays with the at least one container array comprising a first container array that is disposed substantially centrally spaced therebetween, and wherein the magnets are moved to provide the mixing by moving the magnets in the first magnet array forward while rearward moving the magnets in the second magnet array so that adjacent containers in the first container array are alternately exposed to magnetic fields of different pole directions as provided by the magnets in the first and second arrays.

27. Device according to claim 12, wherein the plurality of magnet arrays comprise first and second arrays and the at least one container array comprises a first container array with the first container array disposed substantially centrally spaced therebetween, and wherein the mixing is carried out by oscillating the containers in the first container array, the oscillating step comprises moving the containers in the first container array that containers in the first container array are alternately exposed to changing magnetic fields provided by magnets in the first and second magnet arrays.

28. Method for the isolation of nucleic acid from starting material comprising the following steps:

(a) bringing starting material together with an appropriate lysis buffer and magnetisable particles into at least one container held as one of a plurality of containers in a row that defines a container array that holds the containers in spaced apart alignment, (b) mixing the content of the at least one container by moving first and second magnet arrays, each magnet array comprising a plurality of spaced apart magnets, with the containers in the container array held between the first and second magnet arrays in such a way that the direction of the magnetic field associated with the at least one container is repeatedly reversed for a sufficient amount of time with the magnets at a height that is adjusted to the volume of the sample, (c) collecting the particles at a wall of the container using the magnets, (d) removing most of the sample liquid from the device, (e) adding a sufficient amount of washing buffer to the device, (f) repeating step (b) to (d), (g) adding a suitable amount of elution buffer to the device, (h) drawing the particles down into the tip of the container by moving the magnets to a lower position, (i) optionally heating the container by moving a heatblock into close proximity with the containers, (j) optionally removing an appropriate amount of elution buffer from the device, (k) repeat step (b), (l) move the magnets in a vertical direction to a position above the fluid level, and (m) collect the elution buffer with the isolated nucleic acid container therein.

29. A method of mixing magnetic and/or (super) paramagnetic particles with a fluid comprising:

providing a device with a plurality of containers held in alignment in spaced apart substantially parallel lines of first and second container arrays and a plurality of permanent magnets held in spaced apart substantially parallel lines of first, second and third magnet arrays, with the first container array being positioned between the first and second magnet arrays and the second container array being positioned between the second and third magnet arrays;

introducing magnetic and/or supermagnetic particles into at least one of the containers in the first and/or second container arrays;

moving the magnets in the first magnet array in concert;

concurrently moving the magnets in the second magnet array in concert; and concurrently moving the magnets in the third magnet array in concert whereby the particles in the containers are exposed to varying magnetic fields and directions and attracted to opposing sides of a respective container to thereby mix the fluid therein.

30. A method of mixing magnetic and/or (super) paramagnetic particles with a fluid in a plurality of containers, comprising:

arranging a plurality of magnet arrays and at least one container array having opposing first and second sides so that the arrays are alignably positioned with a first magnet array disposed on a first side of a first container array and a second magnet array is positioned on a second side of the first container array, wherein the first and second magnet arrays comprise a plurality of discrete spaced apart magnets and the first container array is configured to hold a plurality of containers in spaced apart alignment; and moving the magnets in the first and second magnet arrays with respect to the position of the container(s) with the magnets in the first and second magnet arrays configured to travel along substantially parallel travel paths to expose the magnetic particles and/or (super) paramagnetic particles in the containers of the first container array to magnetic fields with different and changing directions.

31. A method according to claim 30, wherein the plurality of magnet arrays comprises first, second, and third magnet arrays, and wherein the at least one container array comprises first and second container arrays with the first container array disposed proximate to and intermediate said first and second magnet arrays and the second container arrays disposed proximate to and intermediate the second and third magnet arrays, whereby the magnets in the first, second and third magnet arrays are repeatedly moved forward and rearward, with the magnet arrays traveling to concurrently mix the particles in the containers.

32. A method according to claim 30, wherein the moving step comprises:

moving the magnets in the first magnet array in concert; and substantially concurrently moving the magnets in the second magnet array in concert whereby the particles in the containers are exposed to varying magnetic fields and directions and attracted to opposing sides of a respective container to thereby mix the fluid therein.

33. A method according to claim 30, wherein the moving step comprises linearly translating magnets in respective magnet arrays about substantially parallel straight line paths so that the magnets in each array move forward and rearward in concert and so that adjacent arrays of magnets move in opposing directions on opposite sides of a respective container array in such a way that a direction of the magnetic field in each container is repeatedly substantially reversed.

34. A method of mixing magnetic and/or (super) paramagnetic particles with a fluid in a plurality of containers, comprising:

arranging a plurality of magnet arrays comprising first, second and third magnet arrays and a plurality of container arrays comprising first and second container arrays, with the container arrays having opposing first and second sides so that a first magnet array is disposed on a first side of the first container array and the second magnet array is positioned on the second side of the first container array and the first side of the second container array and the third magnet array is positioned on the second side of the second container array, wherein the first, second, and third magnet arrays comprise a plurality of discrete linearly aligned spaced apart magnets and the first and second container arrays are configured to hold a plurality of containers in spaced apart linear alignment; and moving the containers in the first container array with respect to the positions of the magnets in the first and second magnet arrays and the containers in the second container array with respect to the positions of the magnets in the second and third magnet arrays to expose the magnetic particles and/or (super) paramagnetic particles in the containers thereof to magnetic fields with different and changing directions to thereby mix the fluid therein.

35. A method according to claim 34, wherein the step of moving the containers comprises retracting the containers along a predetermined travel path.

36. A method according to claim 34, wherein the step of moving the containers comprises oscillating the containers between selected positions.

37. A device for mixing magnetic and/or (super) paramagnetic particles with a fluid in a plurality of containers, comprising:

a plurality of laterally spaced apart magnet arrays including at least first, second and third magnet arrays and a plurality of container arrays including at least first and second container arrays, each container array having opposing first and second sides with the first magnet array being proximately positioned on the first side of the first container array and the second magnet array being proximately positioned on the second side of the first container array and the first side of the second container array and the third magnet array being positioned on the second side of the second container array, wherein the first, second, and third magnet arrays comprise a plurality of discrete spaced apart magnets and the first and second container arrays are configured to hold a plurality of containers in spaced apart alignment; and at least one mechanism that moves the magnets in the first, second and third magnet arrays with respect to the position of the container(s) in the first and second container arrays to concurrently expose the magnetic particles and/or (super) paramagnetic particles in the containers to magnetic fields with different and changing directions.

38. A device for mixing magnetic and/or (super) paramagnetic particles with a fluid in a plurality of containers, comprising:

a plurality of laterally spaced apart magnet arrays including at least first and second magnet arrays and a plurality of container arrays including at least first and second container arrays, each container array having opposing first and second sides with the first magnet array being proximately positioned on the first side of the first container array and the second magnet array being proximately positioned on the second side of the first container array and the first side of the second container array, wherein the magnet arrays comprise a plurality of discrete spaced apart magnets and the first and second container arrays are configured to hold a plurality of containers in spaced apart alignment; and at least one mechanism that moves the containers in the first and second container arrays relative to the magnets in the first and second magnet arrays to concurrently expose the magnetic particles and/or (super) paramagnetic particles in containers in the first and second container arrays to magnetic fields.

39. A device according to claim 38, further comprising a third magnet array with the third magnet array being positioned on the second side of the second container array.

40. A device according to claim 38, wherein the at least one mechanism is configured to advance the containers along a predetermined travel path.

41. A device according to claim 38, wherein the at least one mechanism is configured to retract the containers in concert along a predetermined travel path.

42. A device according to claim 38, wherein the at least one mechanism is configured to oscillate the containers between predetermined positions.

* * * * *

UNITED STATES PATENT AND TRADEMARK OFFICE
CERTIFICATE OF CORRECTION

PATENT NO.    : 6,764,859 B1
DATED         : July 20, 2004
INVENTOR(S)   : Kreuwel et al.

It is certified that error appears in the above-identified patent and that said Letters Patent is hereby corrected as shown below:

Column 9,
Line 21, should read -- array in concert back and forth between magnet arrays. --

Column 10,
Lines 49-50, should read -- array forward while moving the magnets in the second magnet array rearward so that adjacent containers in the first --
Line 61, should read -- container array so that containers in the first container array are --

Signed and Sealed this

Fourteenth Day of December, 2004

JON W. DUDAS
*Director of the United States Patent and Trademark Office*